(12) United States Patent  
Wilbertz et al.

(10) Patent No.: US 8,669,662 B2
(45) Date of Patent: Mar. 11, 2014

(54) FASTENING DEVICE

(71) Applicant: Micronas GmbH, Freiburg (DE)

(72) Inventors: Christoph Wilbertz, Gundelfingen (DE); Heinz-Peter Frerichs, St. Peter (DE); Tobias Kolleth, Freiburg (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 13/691,827

(22) Filed: Dec. 2, 2012

(65) Prior Publication Data

US 2013/0140702 A1 Jun. 6, 2013

Related U.S. Application Data

(60) Provisional application No. 61/567,459, filed on Dec. 6, 2011.

(30) Foreign Application Priority Data

Dec. 2, 2011 (DE) .......................... 10 2011 119 957

(51) Int. Cl.
*H01L 23/48* (2006.01)
(52) U.S. Cl.
USPC ..... 257/770; 257/253; 257/252; 257/E29.242
(58) Field of Classification Search
USPC .................. 257/252, 253, 770, 734, E29.242
See application file for complete search history.

(56) References Cited

U.S. PATENT DOCUMENTS

| 5,137,461 | A | 8/1992 | Bindra et al. |
| 5,432,675 | A | 7/1995 | Sorimachi et al. |
| 5,545,589 | A | 8/1996 | Tomura et al. |
| 6,191,489 | B1 | 2/2001 | Igel et al. |
| 7,439,750 | B2 | 10/2008 | Lindorfer |
| 7,489,023 | B2 | 2/2009 | Pape |
| 2002/0157950 | A1* | 10/2002 | Frerichs .................. 204/416 |

FOREIGN PATENT DOCUMENTS

| DE | 42 39 319 A1 | 4/1993 |
| DE | 199 07 168 C1 | 8/2000 |
| DE | 100 36 178 A1 | 2/2002 |
| DE | 103 16 933 A1 | 10/2004 |
| DE | 103 43 793 A1 | 4/2005 |
| DE | 10 2005 009 163 A1 | 9/2006 |
| DE | 10 2006 053 461 A1 | 5/2008 |
| EP | 1 103 808 A2 | 5/2001 |

* cited by examiner

*Primary Examiner* — Mamadou Diallo
(74) *Attorney, Agent, or Firm* — Muncy, Geissler, Olds & Lowe, P.C.

(57) ABSTRACT

A fastening device is provided that includes a semiconductor body with an integrated circuit, and a dielectric passivation layer formed on the surface of the semiconductor body, and a trace formed underneath the passivation layer, and an oxide layer formed beneath the trace, and a connecting component that forms a frictional connection between a component formed above the passivation layer and the semiconductor body, wherein a formation passing through the passivation layer and the oxide layer and having a bottom surface is formed, and a conductive layer is formed on the bottom surface and the connecting component forms an electrical connection between the conductive layer and the component.

13 Claims, 1 Drawing Sheet

FASTENING DEVICE

This nonprovisional application claims priority to German Patent Application No. 10 2011 119 957.1, which was filed in Germany on Dec. 2, 2011, and to U.S. Provisional Application No. 61/567,459, which was filed on Dec. 6, 2011, and which are both herein incorporated by reference.

BACKGROUND OF THE INVENTION

1. Field of the Invention

The invention relates to a fastening device.

2. Description of the Background Art

It is known from DE 10 2005 009 163 A1, which corresponds to U.S. Pat. No. 7,489,023, that electrodes are formed by conductive adhesive on the passivated surface of a semiconductor body for the purpose of connecting components. In addition, a device and method for producing a microelectronic subassembly are known from DE 10 2006 053 461 A1.

From DE 100 36 178 A1, DE 42 39 319 C2, and EP 1 103 808 B1 are known FET moisture sensors in which the control electrode, which is spaced apart from the channel region by an air gap, is electrically connected to the semiconductor body by means of a bonding method. In addition, the control electrode is frictionally connected to the semiconductor body by means of a clamping device.

Moreover, additional fastening devices are known from DE 199 07 168 C1 (which corresponds to U.S. Pat. No. 6,191,489, which is incorporated herein by reference), U.S. Pat. No. 5,545,589 A, U.S. Pat. No. 5,137,461 A, and U.S. Pat. No. 5,432,675 A.

SUMMARY OF THE INVENTION

It is therefore an object of the invention to provide a fastening device that advances the state of the art.

An embodiment of the invention provides for a fastening device, having a semiconductor body with an integrated circuit, with a dielectric passivation layer formed on the surface of the semiconductor body, a trace formed underneath the passivation layer, and an oxide layer formed beneath the trace, and a connecting component that includes an organic polymer and that forms a frictional connection between a component formed above the passivation layer and the semiconductor body, wherein a formation passing through the passivation layer and the oxide layer and having a bottom surface is formed, and a conductive layer is formed on the bottom surface and/or on a lateral surface of the formation, and the connecting component includes an organic polymer and forms an electrical connection between the conductive layer and the component. It can be noted that the term "connecting component" can be understood to mean such connecting components as are liquid at room temperature. Such connecting components are also referred to as conductive adhesives.

It is an advantage that additional parts of separate components can be connected both electrically and, at the same time, frictionally to the semiconductor body by means of an electrically conductive connecting component. In this context, the term "separate" includes, in particular, components that are not produced in the integrated circuit manufacturing process. Investigations have shown that the novel fastening makes it possible to eliminate a costly mechanical attachment, preferably by means of a lever mechanism or latch mechanism or other fastening component and an additional, separate electrical connection, for example by means of a bond wire. With the new technique, simple, reliable, and economical connections can be created between a semiconductor body and separate components. The term components is understood to mean, in particular, electronic, electromechanical components and parts thereof, e.g. such as a separate control electrode of a gas sensor transistor. In this context, the component can be provided as a first part and the connecting component is provided as a second part of an integrated component formed underneath the passivation layer. Preferably, a signal connection exists between the different parts. In other words, the individual parts of the integrated component stand in operative electrical connection with one another, and only in combination do they form the complete component. In a preferred embodiment, the passivation layer forms a plateau. The component rests on the plateau. In an alternative embodiment, the connecting component forms a large bearing region on the passivation layer outside of the formation, wherein the first component rests on the bearing region. A large bearing region is understood to mean an area whose dimensions are significantly larger than the area of the formation in the plane of the passivation layer.

An additional advantage is that manufacture of the formation is carried out as early as at the so-called wafer level and in this way manufacture of the formation can easily be integrated into the process of manufacturing an integrated circuit. Preferably a dry etching process, in particular the pad window etching process, is used to produce the formation after application of the passivation. Such manufacturing steps following this application are also referred to as back end of line processes.

Further investigations have shown that, depending on the application, even a slight electrical conductivity of the first connecting component below 50 MOhm, extremely preferably below 1 MOhm, suffices to connect, for example, a separate control electrode of an SGFET or CCFET to the base, which is to say to the semiconductor body. In this way, manufacture of the gas sensors can be carried out more economically and reliably. In addition, the overall height is reduced as compared to an implementation with a bond wire on the cover surface of the control electrode.

According to an embodiment, one elevation, preferably a plurality of elevations, is formed on the bottom surface, and in particular they are frustoconical in shape. It is preferred for the elevation to be completely enclosed by the connecting component, and in particular for the elevation to form a material-to-material connection with the connecting component. In this embodiment, the connecting component preferably is implemented as a conductive adhesive.

According to an embodiment, the elevations are designed to be conductive, and in particular it is preferred for the elevations to be implemented as tungsten plugs. An advantage of the elevations is that the connecting component form an especially reliable mechanical and/or electrical connection with the formation and with the bottom surface, in particular. In other words, the tungsten plugs or the elevations increase the surface area and thereby the surface area to be wetted by the connecting component.

According to another embodiment, the conductive layer contains silicon. It is preferred here for the conductive layer to include a doped polysilicon layer and/or a silicide layer. In an alternative embodiment, the conductive layer is composed of a metallic trace or a metal conductor track.

In an embodiment, the connecting component completely fills the formation. In this way, especially reliable connections can be formed between the semiconductor body and the component. It is an advantage that the connecting component seals the formation against contaminants so that no foreign materials enter.

According to an embodiment, it is preferred to implement the formation in the form of a trench or hole. According to an alternative embodiment, it is preferred to implement a part of a lateral surface of the formation with a conductive layer. Investigations have shown that, within the formation, a trace layer is suitable as is also a layer containing silicon, preferably a doped polysilicon layer with an overlying silicide layer. It is advantageous here to implement the silicide layer as tungsten silicide.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
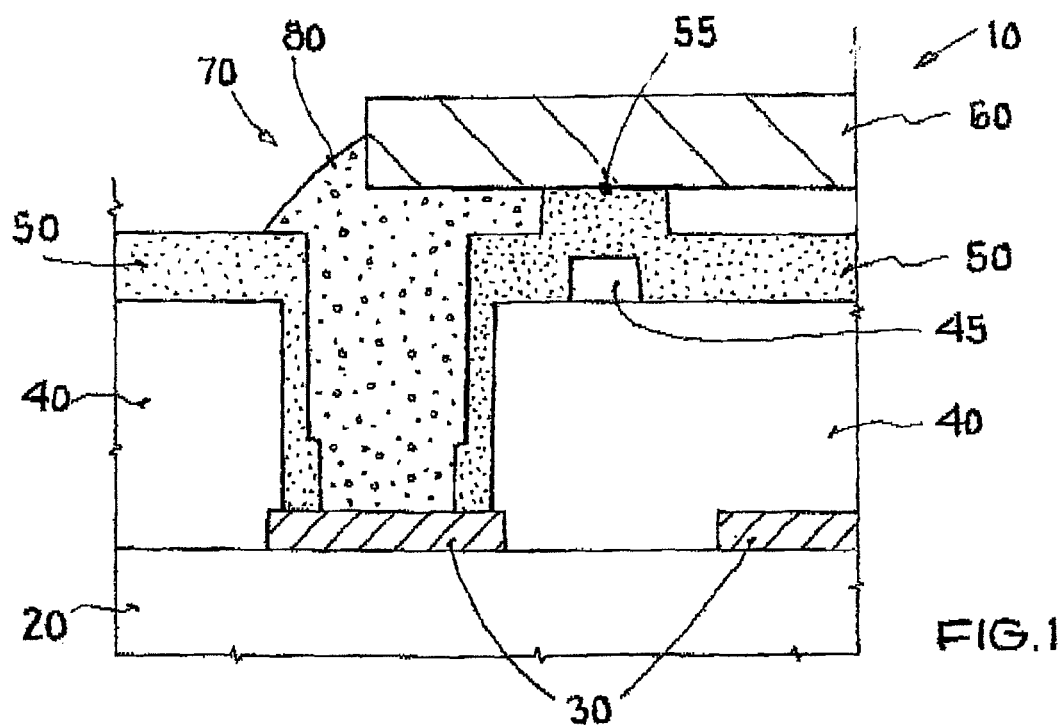
FIG. 1 shows a cross-sectional view of a first embodiment.

The illustration in FIG. 1 shows a cross-sectional view of a first embodiment of a fastening device 10, having a semiconductor body 20, an integrated circuit (not shown), a conductive polysilicon layer 30 formed on the surface of the semiconductor body 20, an oxide layer 40, a trace 45 resting on the oxide layer 40, and a passivation 50. It should be noted that the trace 45 is part of an uppermost trace level that also forms the metal areas for accommodating bond wires. Furthermore, the oxide layer 40 has multiple oxide layers, wherein the oxide layers generally are deposited within the framework of the creation of a multilayer metallization. The passivation 50 preferably is made of silicon nitride and forms a plateau 55 above the trace 45. Arranged to rest on the plateau 55 is a component 60 to be connected to the semiconductor body 20, which is implemented as, for example, the control electrode of a gas sensor. The plateau 55 and the component 60 resting thereon in an interlocking manner together form a groove. In order to reliably connect the component 60 to the semiconductor body 20 in both a frictional manner and electrically, the connecting component 80 completely fills the formation 70 and the groove. In addition, the connecting component 80 also surrounds a part of the lateral surface of the component 60 and a part of the passivation 50 on the surface of the semiconductor body 20. As a result, the connecting component 80 creates both an electrical contact and a frictional connection between the semiconductor body 20 and the component 60. Moreover, the connection is very reliable and resistant to aging. An advantage of the complete filling of the formation 70 is the passivating effect created in this way, which is to say that entry of foreign materials is prevented.

The component 60 preferably is designed to be electrically conductive, at least on the side facing the passivation 50. A formation 70 preferably is designed as a trench-like or hole-like structure and extends through the passivation 50, wherein the polysilicon layer 30 is formed in the bottom region of the formation 70 and the passivation 50 is formed on the walls of the formation 70. This makes it evident that the formation 70 has been applied by means of an etching process prior to the deposition of the passivation 50. Next, the polysilicon layer 30 is exposed in the bottom region of the formation 70 using a so-called pad window etching process. In an alternative embodiment that is not shown, the formation 70 can also be produced after deposition of the passivation 50. In this variation, no passivation layer 50 is formed on the lateral surfaces of the formation 70.

As shown in the representation in FIG. 1, the formation 70 is filled by the connecting component 80. The connecting component 80 partially encompasses the component 60 at a lateral surface, and forms a material-to-material connection with the component 60 and with the surface of the formation.

Figure 2:
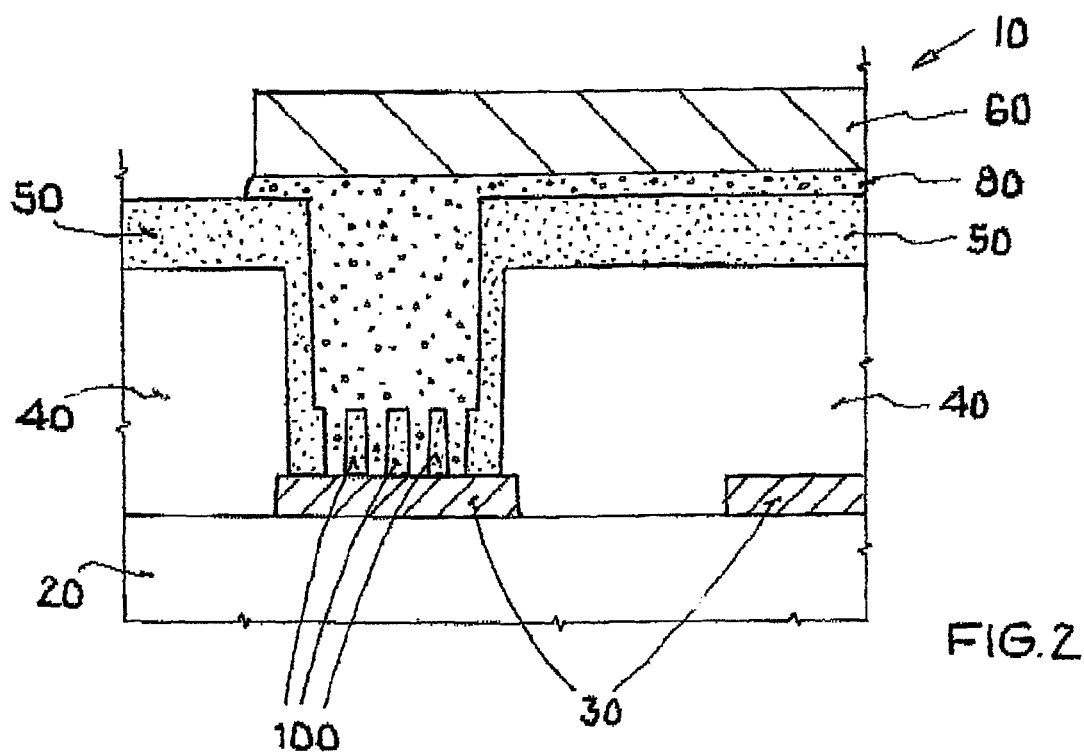
FIG. 2 shows a cross-sectional view of a second embodiment.

A second embodiment is shown in the illustration in FIG. 2. In the following, only the differences from the embodiment shown in FIG. 1 shall be explained. The component 60 completely covers the formation 70. Outside of the formation 70, the connecting component 80 is formed between the component 60 and the passivation 50, which is to say that a large bearing area for the component 70 is formed. A plurality of frustoconical elevations, which preferably are implemented as tungsten plugs 100, are arranged on the bottom surface of the formation 70 or on the polysilicon layer 30. The tungsten plugs 100 form an interlocking and frictional connection with the base, which preferably has a silicide layer that is not shown, most preferably a tungsten silicide layer. The tungsten plugs 100 are each encased in the first connecting component 80. In this way, an especially strong and reliable connection is formed between the connecting component 80 and the bottom region of the formation 70.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A fastening device comprising:
a semiconductor body with an integrated circuit;
a dielectric passivation layer provided on the surface of the semiconductor body;
a trace provided underneath the passivation layer;
an oxide layer provided beneath the trace;
a connecting component that forms a frictional connection between a component arranged above the passivation layer and the semiconductor body;
a formation passing through the passivation layer and the oxide layer, the formation having a bottom surface; and
a conductive layer provided on the bottom surface and/or on a lateral surface of the formation, the connecting component having an organic polymer and forms an electrical connection between the conductive layer and the component,
wherein the component is provided as a first part and the connecting component is provided as a second part of an integrated component formed underneath the passivation layer.

2. The fastening device according to claim 1, wherein one elevation is formed on the bottom surface.

3. The fastening device according to claim 2, wherein a plurality of elevations are formed on the bottom surface.

4. The fastening device according to claim 2, wherein the elevation is implemented as a tungsten plug.

5. The fastening device according to claim 2, wherein the elevation is completely enclosed by the connecting component.

6. The fastening device according to claim 2, wherein the elevation forms a material-to-material connection with the connecting component.

7. The fastening device according to claim 1, wherein the conductive layer contains silicon.

8. The fastening device according to claim 1, wherein the conductive layer is made of a doped polysilicon layer and a silicide layer.

9. The fastening device according to claim 1, wherein the conductive layer is composed of a metallic trace.

10. The fastening device according to claim 1, wherein the connecting component completely fills the formation.

11. The fastening device according to claim 1, wherein the connecting component contains a conductive adhesive.

12. The fastening device according to claim 1, wherein the component is a control electrode of a gas sensor transistor.

13. The fastening device according to claim 1, wherein the passivation layer forms a plateau, and the component rests on the plateau, or wherein the connecting component outside of the formation forms a large bearing region on the passivation layer, and the component rests on the bearing region.

\* \* \* \* \*